United States Patent
Soga et al.

(10) Patent No.: US 7,316,675 B2
(45) Date of Patent: Jan. 8, 2008

(54) DISPOSABLE PANTS-TYPE WEARING ARTICLE

(75) Inventors: Hiroyuki Soga, Kagawa-ken (JP); Satoru Tange, Kagawa-ken (JP); Yuko Matsuda, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 11/336,959

(22) Filed: Jan. 23, 2006

(65) Prior Publication Data

US 2006/0167426 A1      Jul. 27, 2006

(30) Foreign Application Priority Data

Jan. 24, 2005    (JP)    ............................. 2005-016072

(51) Int. Cl.
 *A61F 13/15*    (2006.01)
(52) U.S. Cl. ........................... 604/385.25; 604/385.27; 604/358; 604/381; 604/378; 604/385.23
(58) Field of Classification Search ........... 604/385.25, 604/385.01, 387, 391, 385.27, 358, 381, 604/378, 385.23

See application file for complete search history.

(56) References Cited

U.S. PATENT DOCUMENTS

| 3,650,273 | A | * | 3/1972 | Schaar | ............................ 2/402 |
| 3,776,233 | A | * | 12/1973 | Schaar | .................. 604/385.23 |
| 3,848,599 | A | * | 11/1974 | Schaar | .................. 604/385.23 |
| 3,943,930 | A | * | 3/1976 | Schaar | ........................ 604/365 |
| 4,573,990 | A | * | 3/1986 | Ohsaki | ................ 604/385.201 |
| 5,440,764 | A | * | 8/1995 | Matsushita | ...................... 2/401 |
| 5,449,353 | A | * | 9/1995 | Watanabe et al. | ....... 604/385.27 |
| 5,836,931 | A | | 11/1998 | Toyoda et al. | |
| 6,638,260 | B2 | * | 10/2003 | Mishima | ................ 604/385.01 |

FOREIGN PATENT DOCUMENTS

JP           4-289201 A        10/1992

* cited by examiner

*Primary Examiner*—Tatyana Zalukaeva
*Assistant Examiner*—Ginger Chapman
(74) *Attorney, Agent, or Firm*—Lowe, Hauptman, Ham & Berner LLP

(57) ABSTRACT

A disposable pants-type wearing article includes an inner sheet, an outer sheet and an intermediate sheet having two or more plastic film strips sandwiched between the inner sheet and the outer sheet. The film strips are overlapped one another to define an overlapped region dimensioned to be 10 to 100 mm in a longitudinal direction of the wearing article and extend in a transverse direction to the vicinity of leg-surrounding elastic members.

1 Claim, 5 Drawing Sheets

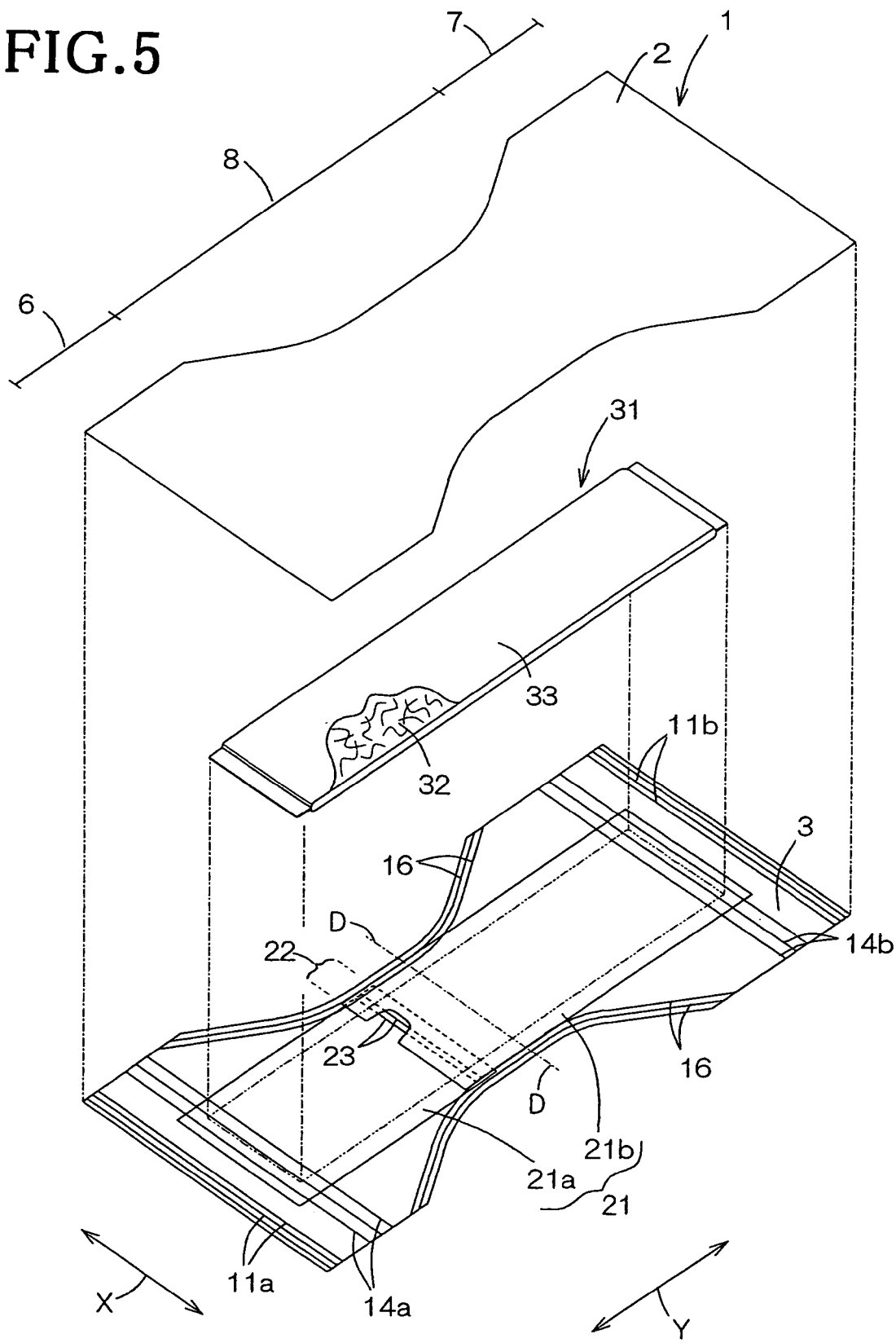

DISPOSABLE PANTS-TYPE WEARING ARTICLE

RELATED APPLICATIONS

The present application is based on, and claims priority from, Japanese Application Number 2005-16072, filed Jan. 24, 2005, the disclosure of which is hereby incorporated by reference herein in its entirety.

BACKGROUND OF THE INVENTION

The present invention relates to disposable pants-type wearing articles adapted to be smoothly put on a wearer's body.

Conventionally, the disposable wearing articles have been proposed in various forms such as the disposable pair of pants and the disposable pants-type diapers. One example of such disposable wearing articles is the disposable pair of briefs disclosed in Japanese Patent Application Publication No. 1992-289201A (Citation 1). In this disposable pair of briefs, the waist-opening and the leg-openings are respectively provided with the band-like elastic members attached thereto along the respective peripheral edges thereof. The elastic members for the waist-opening are arranged so as to extend in a transverse direction and to be spaced one from another in a longitudinal direction from the peripheral edge of the waist-opening toward the crotch region over a wide area. Such an arrangement of the waist-surrounding elastic members ensures desired fitness of the briefs around the wearer's waist over the correspondingly wide area.

However, such a conventional pair of briefs has often caused inconvenience for a mother intending to put it on her baby due to an excessive contraction of the elastic members. Specifically, a contraction of the elastic members necessarily results in deformation of the pair of briefs and, if such a contraction is excessive, the pair of briefs may be deformed to the extent making it difficult for the mother to pick out the waist-opening as well as the leg-openings. Consequently, a lot of time may be required for the mother to put the pair of briefs on her baby's body. Even after the mother has picked out the waist-opening and sufficiently spread out, it may be difficult for the mother to pick out the leg-openings each remaining deformed to the minimum size.

SUMMARY OF THE INVENTION

In view of the problem as has been described above, it is an object of the present invention to improve a disposable pants-type wearing article provided with band-like elastic members attached thereto in a stretched state in waist- and leg-surrounding directions, respectively, improved so that the article can be smoothly put on the wearer's body.

The object set forth above is achieved, according to the present invention, a disposable pants-type wearing article comprising: a front waist region; a rear waist region; a crotch region; an inner sheet defining a surface destined to come in contact with a wearer's skin; an outer sheet defining a surface destined to come in contact with a garment; an intermediate sheet formed by a plastic film strip sandwiched between the inner sheet and the outer sheet; a plurality of band-like elastic members extending in a stretchable fashion in a waist-surrounding direction in at least one of the front and rear waist regions; a plurality of leg-surrounding elastic members extending in stretchable fashion in a leg-surrounding direction in the crotch region along peripheral edges of respective leg-openings.

The intermediate sheet including an overlapped region in which a plurality of the plastic film strips are overlapped one another in width of 10 to 100 mm as measured in a longitudinal direction of the wearing article; and the overlapped region extending in the transverse direction to the vicinity of the leg-surrounding elastic members.

According to the first preferred embodiment of the present invention, the overlapped regions is defined in a zone of the crotch region put aside toward the front waist region as well as in a zone of the crotch region put aside toward the rear waist region.

According to the second preferred embodiment of the present invention, the plastic film strips are adhesively bonded or welded one to another in the overlapped region.

According to the third preferred embodiment of the present invention, the inner sheet is liquid-pervious while the intermediate sheet is liquid-impervious and a block of bodily fluid absorbent material is sandwiched between the inner sheet and the intermediate sheet in the crotch region in such a manner that each of the overlapped regions extends outward at least 10 mm beyond side edges of the block opposed in the transverse direction.

The disposable pants-type wearing article according to the present invention includes the overlapped region of the intermediate sheet formed in the crotch region and the overlapped region extends in the transverse direction of the pants-type wearing article to the vicinity of the leg-surrounding elastic members for a pair of the leg-openings. This unique arrangement allows the overlapped region to restrain deformation possibly occurring in the vicinity of the leg-openings and thereby to prevent the leg-openings from being significantly twisted and/or from being excessively closed even when the elastic members extending in the waist-surrounding direction as well as the elastic members extending in the leg-surrounding direction contract. With such pants-type wearing article, the leg-openings are readily picked out when it is desired to put the article on the article wearer's body.

The disposable pants-type wearing article of the first preferred embodiment includes the overlapped regions of the intermediate sheet are provided on both the front and rear sides of the pants-type wearing article. With such unique arrangement, a deformation possibly occurring in the vicinity of the leg-openings due to contraction of the elastic members can be effectively restrained not only on the front side but also on the rear side of the pants-type wearing article.

In the disposable pants-type wearing article of the second preferred embodiment, a plurality of the plastic film strips constituting the intermediate sheet are overlaid and integrally bonded one to another in the respective overlapped regions. Compared to the case in which the film strips are not integrally bonded one to another, this wearing article further improves the effect to restrain deformation possibly occurring in the vicinity of the leg-openings since it is unlikely that the intermediate sheet might be readily out of alignment or folded due to contraction of the elastic members.

The disposable pants-type wearing article of the third preferred embodiment includes the block of bodily fluid absorbent material sandwiched between the inner sheet and the intermediate sheet in the crotch region and the intermediate sheet is liquid-impervious. The article having such construction can be used as the disposable diaper adapted to be smoothly put on the article wearer's body.

BRIEF DESCRIPTION OF THE DRAWINGS

FIG. 5 is a view similar to FIG. 2, showing this another preferred embodiment of the invention.

DETAILED DESCRIPTION OF THE PREFERRED EMBODIMENTS

Details of a disposable pants-type wearing article according to the present invention will be more fully understood from the description of a disposable pair of pants as one embodiment of the invention given hereunder with reference to the accompanying drawings.

Figure 1:
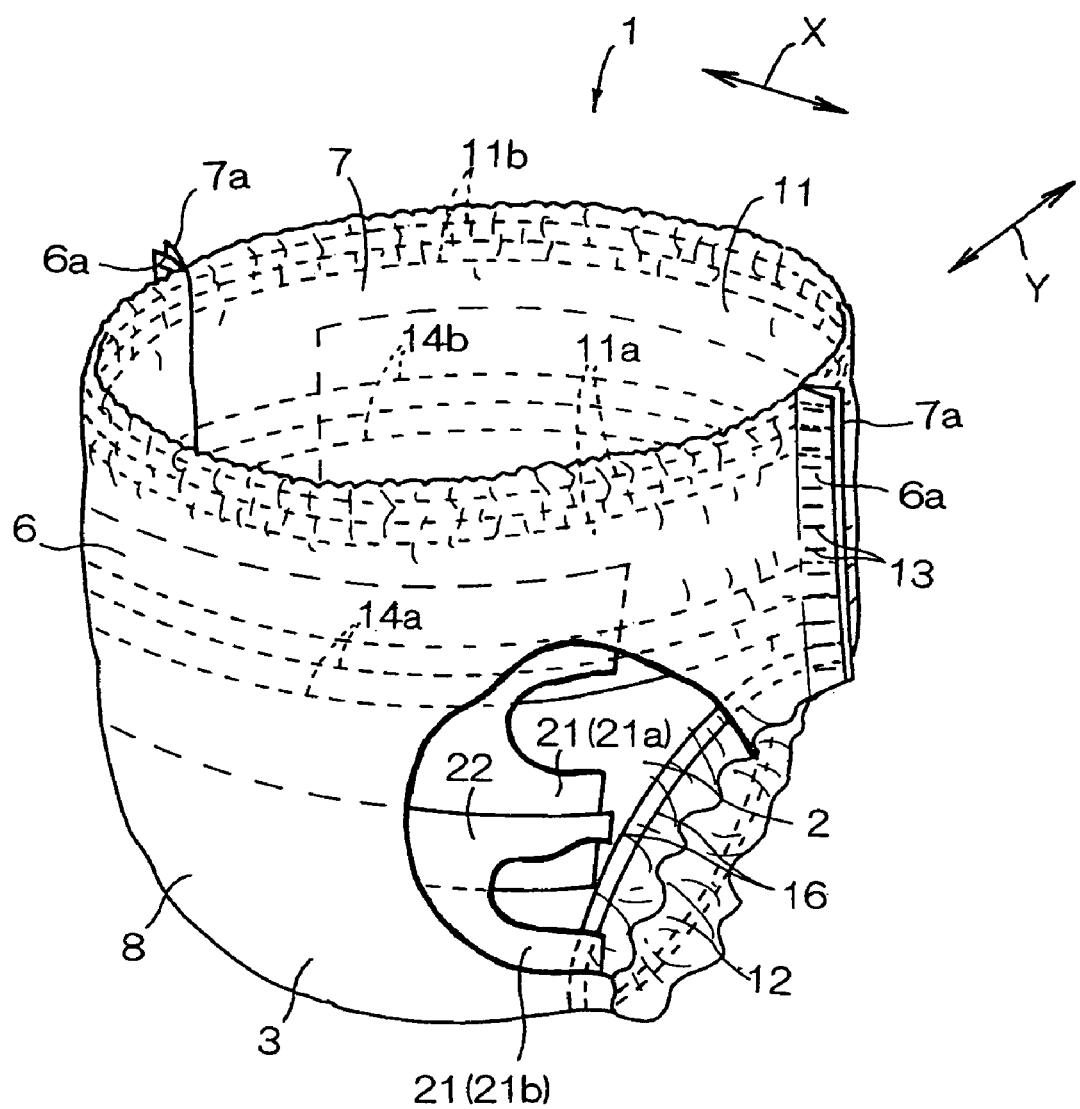
FIG. 1 is a partially cutaway perspective view showing a typical embodiment of the pants according to the invention as put on the wearer's body.

FIG. 1 is a partially cutaway perspective view showing disposable pants 1. The pants 1 present a pants-like appearance and includes an inner sheet 2 defining a surface destined to come in contact with the wearer's skin (not shown) and an outer sheet 3 defining a surface destined to come in compact with a garment. The pants 1 have a front waist region 6, a rear waist region 7 and a crotch region 8. The inner sheet 2 and the outer sheet 3 are overlapped and bonded to each other by means of a hot melt adhesive (not shown) intermittently applied thereon. The front and rear waist regions 6, 7 are put flat and welded together along respective opposite side edges 8, 9 at a plurality of bonding spots 13 arranged intermittently in a vertical direction as viewed in FIG. 1 to form a waist-opening 11 and cooperate with the crotch region 8 to form a pair of leg-openings 12. In the front and rear waist regions 6, 7, first band-like waist-surrounding elastic members 11a, 11b extend in the waist-surrounding direction in the vicinity of a peripheral edge of the waist-opening 11 while, between the peripheral edge of the waist-opening 11 and peripheral edges of the respective leg-openings 12, a plurality of second band-like waist-surrounding elastic members 14a, 14b extend in the waist-surrounding direction. In the crotch region 8, a plurality of leg-surrounding elastic members 16 extend along the peripheral edges of the respective leg-openings 12. These first and second waist-surrounding elastic members 11a, 11b, 14a, 14b as well as leg-surrounding elastic members 16 are sandwiched between the inner sheet 2 and the outer sheet 3 and bonded in a stretched state to at least one of these sheets 2, 3. Between the inner sheet 2 and the outer sheet 3, an intermediate sheet 21 made of plastic film is also interposed. This intermediate sheet 21 extends primarily over the crotch region 8 and also into the front waist region 6 as well as into the rear waist region 7. Specifically, the intermediate sheet 21 includes a front intermediate sheet 21a extending over the front waist region 6 and a part of the crotch region 8 located aside toward the front waist region 6 and a rear intermediate sheet 21b extending over the rear waist region 7 and a part of the crotch region 8 located aside toward the rear waist region 7. These two intermediate sheets 21a, 21b are overlapped each other in the vicinity of a front boundary of the crotch region 8 so as to define an overlapped region 22.

Figure 2:
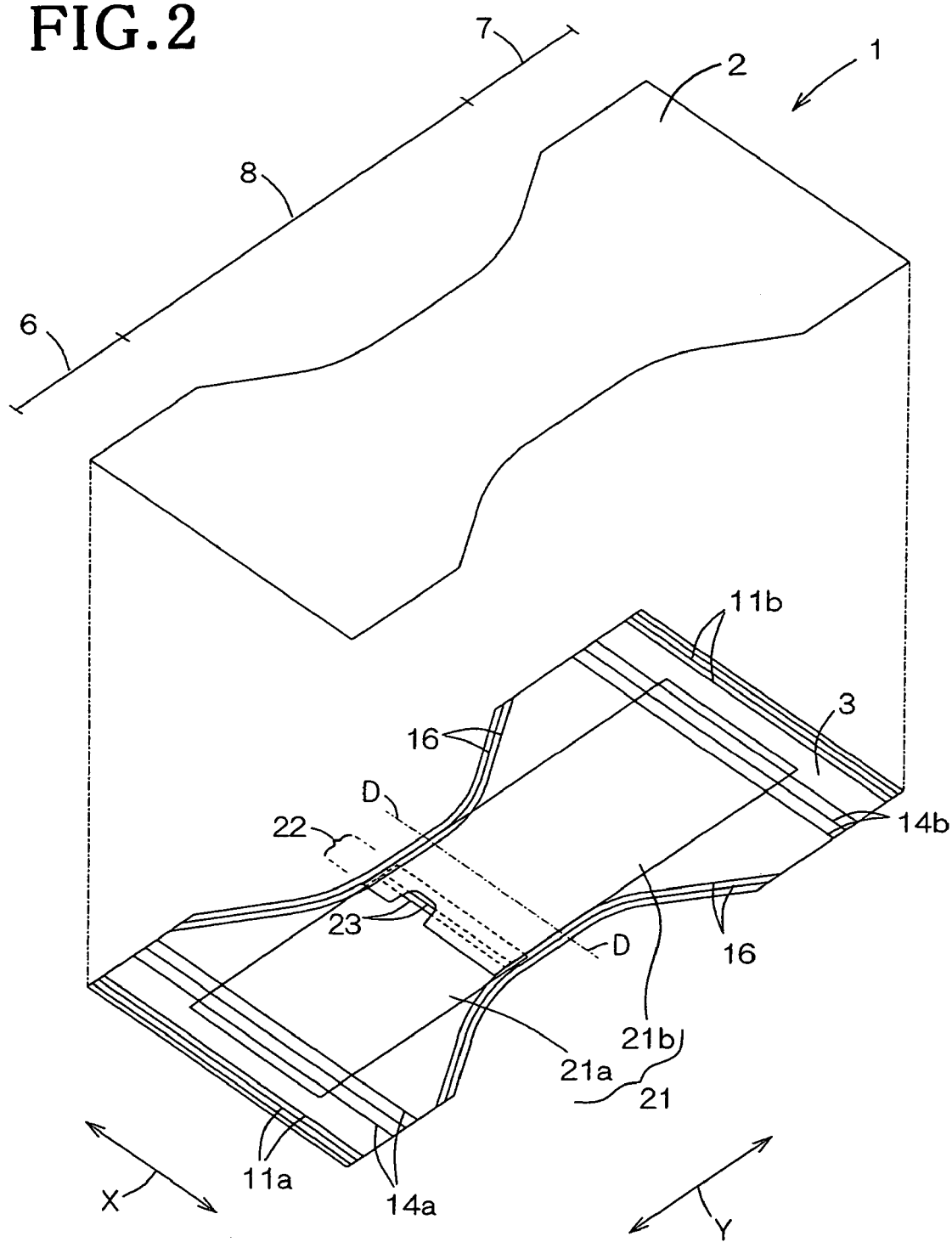
FIG. 2 is an exploded perspective view of the pants as partially cut away.

FIG. 2 is an exploded perspective view of the pants 1 as partially cut away. FIG. 2 shows the pants 1 developed from the state of FIG. 1 in a transverse direction of the pants 1 indicated by a double-headed arrow X as well as in a longitudinal direction of the pants 1 orthogonal to the direction X and indicated by a double-head arrow Y. A center line bisecting a dimension in the longitudinal direction Y is designated by D-D. FIG. 2 illustrates the inner sheet 2 and the outer sheet 3 of the pants 1 having been peeled off and separated from each other in a vertical direction as viewed in FIG. 2 and illustrates the elastic members 11a, 11b, 14a, 14b respectively attached in a stretched state to the outer sheet 3. The intermediate sheet 21 primarily extends over the crotch region 8 and further into the front and rear waist regions 6, 7. In a central zone of the pants 1 defined in the vicinity of the center line D-D, the intermediate sheet 21 extends in the transverse direction X so as to overlap the leg-surrounding elastic members 16 and is intermittently bonded to the outer sheet 3, preferably to both of the outer sheet 3 and the inner sheet 2 by means of a hot melt adhesive (not shown). The overlapped region 22 of the intermediate region 22 preferably has a dimension in a range of 10 to 50 mm for the baby pants 1 and in a range of 20 to 100 mm for the adult pants 1 as measured in the longitudinal direction Y. While no particular location is specified with respect to the overlapped region 22 in the crotch region 8, such overlapped region 22 is located in the crotch region 8 put aside toward the front waist region 6 in the pants 1 as shown in FIGS. 1 and 2. In the overlapped region 22, the front intermediate sheet 21a and the rear intermediate sheet 21b are bonded to each other by means of at least one band-shaped bonding line 23 of hot melt adhesive extending across the full width of these sheets 21a, 21b and the band-shaped bonding line 23 preferably has a width in a range of 0.5 to 1.5 mm. The overlapped region 22 is bonded to one of the inner sheet 2 and the outer sheet 3, preferably to both of these sheets 2, 3 by means of a hot melt adhesive (not shown). Without departing from the scope of the invention, the band-shaped bonding line 23 as illustrated may be replaced by a band-shaped welding line formed in these sheets 21a, 21b themselves made of thermoplastic film strips. Furthermore, the present invention may be implemented in a manner different from the illustrated embodiments, in which the pair of pants dispenses with the waist-surrounding elastic members in any one of the front and rear waist regions 6, 7. The band-shaped bonding line 23 illustrated to be rectilinear in FIG. 1 may be replaced by a band-shaped line undulating to describe sine curve.

Also the pair of pants 1 constructed as illustrated by FIGS. 1 and 2 tends to shrink significantly in the transverse direction X and particularly the waist-opening 11 tends to be closed to the minimum size as the elastic members 11a, 11b, 14a, 14b, 16 respectively contract. However, in the vicinity of the leg-openings 12, the overlapped region 22 of the intermediate sheet 21 is effective to restrain contraction of the crotch region 8 in the transverse direction X as well as in the leg-surrounding direction so that this overlapped region 22 may prevent the leg-openings 12 from being deformed so as to twist and/or to be closed to an unacceptably small size. Consequentially, when the mother puts the pants 1 on her baby's body, the leg-openings 12 readily get into the mother's eye upon appropriately spreading out the waist-opening 11 with her left and right hands and she can smoothly put the pants 1 on her baby's body. The respective leg-openings 12 are covered with the overlapped region 22 only along limited parts of the respective peripheral edges and therefore it is unlikely that the overlapped region 22 might interfere with a stretch and contraction of the leg-surrounding elastic members 16 all over the peripheral edges.

In the pants 1 as has been described above, the inner sheet 2 as well as the outer sheet 3 may be formed by a sheet material such as a nonwoven or woven fabric, a thermoplastic film or thermoplastic net. In order to ensure that a high effect is obtained by incorporating the overlapped region 22, the inner sheet 2 and the outer sheet 3 are preferably formed by a nonwoven fabric made of thermoplastic synthetic fibers having a basis weight in a range of 10 to 100 g/m$^2$ and providing the wearer with a soft and agreeable feeling to wear. The intermediate sheet 21 is preferably formed by flexible film made of thermoplastic material such as polyethylene, polypropylene or polyester, or made of thermoplastic elastomer. The front intermediate sheet 21a and the rear intermediate sheet 21b forming together the intermediate sheet 21 are overlapped and bonded to each other to define the overlapped region 22 in which the intermediate sheet 21 has a relatively high rigidity making it difficult to fold the intermediate sheet 21 along a line extending in a direction orthogonal to the center line D-D. This high rigidity enables the overlapped region 22 to restrain deformation of the inner sheet 2 and the outer sheet 3. Result of the rigidity measurement conducted by Method A in conformity with JIS 1096-1096 6.19.1 (Method A: 45° cantilever method) suggested that the preferred overlapped region 22 of the intermediate sheet 21 should exhibit a rigidity 10% or more higher than the remainder of the intermediate sheet 21 can exhibit. For this rigidity measurement, respective samples each dimensioned to be 150 mm as measured in the transverse direction X and 20 mm as measured in the longitudinal direction Y were cut out from the overlapped region 22 and the remainder. These samples were cut away from the intermediate sheet 21 with attention that the distribution of adhesive should not be uneven in the longitudinal direction Y, for example, along the bonding line 23.

Figure 3:
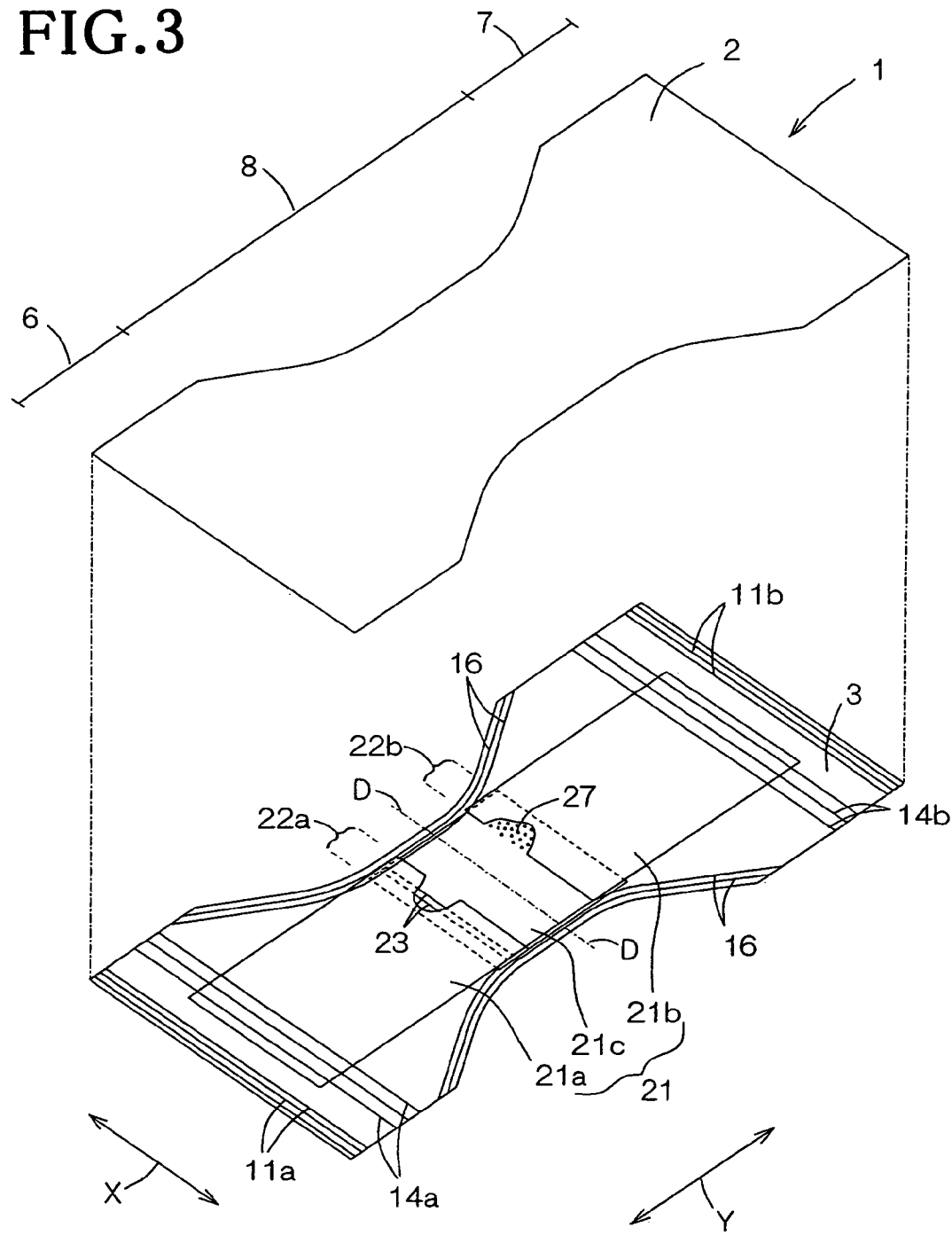
FIG. 3 is a view similar to FIG. 2, showing one preferred embodiment of the invention.

FIG. 3 is a view similar to FIG. 2, showing one preferred embodiment of the invention. This embodiment is distinguished from the previously described embodiment in that the intermediate sheet 21 comprises the front intermediate sheet 21a laid aside toward the front waist region 6, the rear intermediate sheet 21b laid aside toward the rear waist region 7 and a connecting intermediate sheet 21c laid in the crotch region 8 so as to connect those two intermediate sheets 21a, 21b. The front intermediate sheet 21a and the connecting intermediate sheet 21c are overlapped each other in front of the center line D-D bisecting the dimension of the outer sheet 3 in the longitudinal direction and bonded to each other by means of two bonding lines 23 of hot melt adhesive so as to define a front overlapped region 22a. The rear intermediate sheet 21b and the connecting intermediate sheet 21c are overlapped behind the center line D-D and bonded to each other by means of a plurality of dots 27 formed by hot melt adhesive so as to define a rear overlapped region 22b. These two overlapped regions 22a, 22b function to prevent the leg-openings 12 from being excessively closed on front and rear sides of the pants, respectively. In the front overlapped region 22a, the band-shaped bonding line 23 of hot melt adhesive extending in the transverse direction X makes it difficult to fold the front overlapped region 22a in the direction orthogonal to the transverse direction X. In the rear overlapped region 22b, a hot adhesive applied as a plurality of dots 27 spaced one from another is not so effective to restrain deformation of the inner and outer sheets 2, 3 as a hot melt adhesive applied on the front overlapped region 22a is. As will be obvious from this fact, the bonding line, for example, the bonding line 23 continuously extending in the transverse direction X is preferably used to connect the sections constituting the intermediate sheet 21 one to another in the overlapped region 22 and/or in the overlapped regions 22a, 22b of the pants 1.

Figure 4:
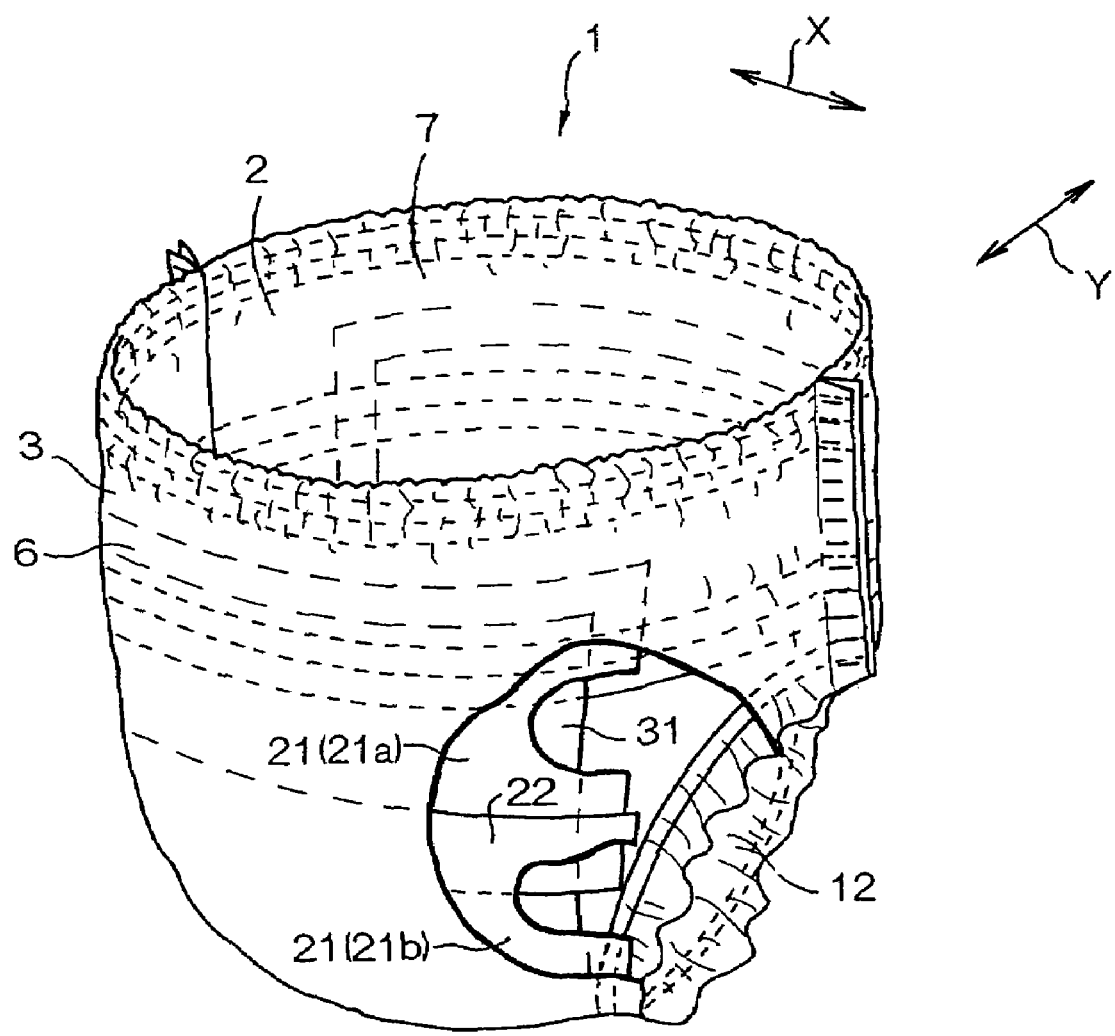
FIG. 4 is a view similar to FIG. 1 showing another preferred embodiment of the invention.

FIGS. 4 and 5 are views similar to FIGS. 1 and 2, respectively, showing another preferred embodiment of the invention. Pants 1 shown in FIGS. 4 and 5 are adapted to be used as a disposable diaper and includes a block 31 of bodily fluid absorbent material sandwiched between the inner sheet 2 and the intermediate sheet 21. The block 31 is formed by aggregated fluff pulp 32 wrapped with a tissue paper 33 having a significant liquid-permeability and a liquid-diffusivity or by a mixture of fluff pulp 32 and super-absorbent polymer particles (not shown) wrapped with a tissue paper 33. The block 31 has dimensions in the longitudinal direction Y and the transverse direction X smaller than the corresponding dimensions of the intermediate sheet 21 so that the intermediate sheet 21 may extend outward beyond a peripheral edge of the block 31. The particularly preferred block 31 has edges opposed to each other in the transverse direction X spaced inward from the corresponding edges of the intermediate sheet 21 by at least 10 mm. In other words, the intermediate sheet 21 extends outward in the transverse direction X beyond the side edges of the block 31. The intermediate sheet 21 is shaped in the same manner as in the embodiment shown in FIG. 2 and liquid-impervious, more preferably air-permeable but liquid-impervious to ensure that the intermediate sheet 21 is able to prevent any amount of bodily fluids from leaking beyond the peripheral edge of the block 31. In this way, the intermediate sheet 21 in this embodiment functions not only as a leak-barrier sheet but also functions to restrain a possibility that the inner sheet 2 and/or the outer sheet 3 might be deformed in the vicinity of the leg-openings 12, i.e., where the overlapped region 22 extends outward beyond the side edges of the block 31, resulting in that the leg-openings 12 might be twisted and/or excessively closed. In the pants 1 according to this embodiment, the outer sheet 3 may be formed, for example, by air-permeable, breathable and liquid-pervious or breathable but liquid-impervious nonwoven or woven fabric or plastic film.

Without departing from the scope of the invention, the number of the overlapped regions 22 to be provided in the crotch region 8 so as to be spaced one from another in the longitudinal direction Y is not specified so far as these overlapped regions 22 effectively restrain deformation of the inner sheet 2 and the outer sheet 3 in the vicinity of the leg-openings 12 but do not significantly affect the desired stretch and contraction of the leg-surrounding elastic members 16. For example, the overlapped region 22 defined in front of the center line D-D as shown in FIG. 2 may be replaced by the overlapped region 22 defined behind the center line D-D. According to the present invention, the overlapped region 22 is defined on the inner surface of the outer sheet 3 to avoid an anxiety that the overlapped region 22 might affect an appearance of the pants 1. By use of a liquid-impervious sheet material, the pants 1 shown in FIG. 1 will be useful as pants serving as a chassis for a urine absorbent pad or a blood absorbent pad.

The present invention enables production of the pants-type wearing article improved so that the leg-openings can be readily pick out when it is desired to put the article on the wearer's body.

The entire discloses of Japanese Patent Application No. 2005-16072 filed on Jan. 24, 2005 including specification, drawings and abstract are herein incorporated by reference in its entirety.

What is claimed is:

1. A disposable pants-type wearing article, comprising:
a front waist region;
a rear waist region;
a crotch region;
an inner sheet defining a surface adapted to come in contact with a wearer's skin;
an outer sheet defining a surface adapted to come in contact with a garment;
an intermediate sheet formed by a plurality of plastic film strips sandwiched between said inner sheet and said outer sheet;
a plurality of band-like elastic members extending in a stretchable fashion in a waist-surrounding direction in at least one of said front and rear waist regions;
a plurality of leg-surrounding elastic members extending in stretchable fashion in a leg-surrounding direction in said crotch region along peripheral edges of respective leg-openings;
said intermediate sheet including an overlapped region in which the plastic film strips overlap one another in a width of 10 to 100 mm as measured in a longitudinal direction of said wearing article; and
said overlapped region extending in a transverse direction to a vicinity of said leg-surrounding elastic members;
wherein
the intermediate sheet includes two overlapped regions;
a front one of the overlapped regions is closer to the front waist region than to the rear waist region and consists of a front one and a middle one of the plastic film strips, said front and middle plastic film strips overlapping and bonded to each other in said front overlapped region by a bonding line that extends continuously in the transverse direction of the article from one end of the front overlapped region to an opposite end of the front overlapped region; and
a rear one of the overlapped regions is closer to the rear waist region than to the front waist region and consists of a rear one and the middle one of the plastic film strips, said rear and middle plastic film strips overlapping and bonded to each other in said rear overlapped region.

* * * * *